(12) United States Patent
Ellis (10) Patent No.: US 11,357,618 B2
(45) Date of Patent: Jun. 14, 2022

(54) INTRAOCULAR LENSES WITH SHAPE-CHANGING OPTICS

(71) Applicant: JelliSee Ophthalmics Inc., McLean, VA (US)

(72) Inventor: Forrest J. Ellis, McLean, VA (US)

(73) Assignee: JelliSee Orphthalmics Inc., McLean, VA (US)

( * ) Notice: Subject to any disclaimer, the term of this patent is extended or adjusted under 35 U.S.C. 154(b) by 0 days.

(21) Appl. No.: 17/378,681

(22) Filed: Jul. 17, 2021

(65) Prior Publication Data

US 2022/0015894 A1 Jan. 20, 2022

Related U.S. Application Data

(60) Provisional application No. 63/053,134, filed on Jul. 17, 2020.

(51) Int. Cl.
| | |
|---|---|
| *A61F 2/16* | (2006.01) |
| *C08K 5/549* | (2006.01) |
| *C08L 25/16* | (2006.01) |
| *C08L 83/04* | (2006.01) |

(52) U.S. Cl.
CPC ............ *A61F 2/1635* (2013.01); *A61F 2/161* (2015.04); *A61F 2/1605* (2015.04); *A61F 2/1618* (2013.01); *C08K 5/549* (2013.01); *C08L 25/16* (2013.01); *C08L 83/04* (2013.01); *A61F 2002/169* (2015.04); *A61F 2210/0071* (2013.01); *A61F 2210/0076* (2013.01)

(58) Field of Classification Search
CPC ....... A61F 2/1635; A61F 2/1605; A61F 2/161
See application file for complete search history.

(56) References Cited

U.S. PATENT DOCUMENTS

| | | |
|---|---|---|
| 7,857,848 B2 | 12/2010 | Mentak |
| 7,985,253 B2 | 7/2011 | Cumming |
| 8,216,310 B2 | 7/2012 | Hu et al. |
| 8,232,363 B2 | 7/2012 | Hu et al. |
| 8,481,667 B2 | 7/2013 | Hu et al. |
| 8,530,590 B2 | 9/2013 | Hu et al. |
| 8,900,298 B2 | 12/2014 | Anvar et al. |

(Continued)

OTHER PUBLICATIONS

PCT International Search Report and Written Opinion for corresponding International Application Serial No. PCT/US2021/042114, dated Nov. 9, 2021, pp. 1-13.

*Primary Examiner* — Jerrah Edwards
*Assistant Examiner* — Aren Patel
(74) *Attorney, Agent, or Firm* — Tarolli, Sundheim, Covell & Tummino LLP (57) ABSTRACT

An intraocular lens (IOL) with a shape-changing optic is provided. The IOL includes an anterior face and/or a posterior face that is fabricated from a poly(dimethylsiloxane) elastomer having a durometer between about 30 Shore A to about 50 Shore A. A chamber is located between the anterior face and the posterior face and includes a silicone oil including diphenyl siloxane and dimethyl siloxane units. The silicone oil has a maximum viscosity of about 700 $mm^2/s$ at 25° C. and has a mean molecular weight of less than about 3,000 Daltons. An IOL is also provided that includes an anterior face and/or posterior face that is fabricated from a polysiloxane that is at least 99% poly(dimethylsiloxane) elastomer.

10 Claims, 7 Drawing Sheets

(56) References Cited

U.S. PATENT DOCUMENTS

| | | |
|---|---|---|
| 9,156,949 B2 | 10/2015 | Hu et al. |
| 9,216,558 B2 * | 12/2015 | Padsalgikar ............ B32B 37/06 |
| 9,339,373 B2 | 5/2016 | Hu et al. |
| 9,534,088 B2 | 1/2017 | Hu et al. |
| 10,526,353 B2 | 1/2020 | Silvestrini |
| 10,709,549 B2 | 7/2020 | Argento et al. |
| 10,835,383 B2 | 11/2020 | Frankle et al. |
| 10,898,316 B2 | 1/2021 | Ellis |
| 10,980,629 B2 | 4/2021 | Anvar et al. |
| 2011/0208301 A1 * | 8/2011 | Anvar ................... C08G 77/34 623/6.13 |
| 2014/0309735 A1 * | 10/2014 | Sohn ................... A61F 2/1648 623/6.34 |
| 2017/0342096 A1 * | 11/2017 | Silvestrini .............. C08G 77/24 |
| 2018/0153682 A1 * | 6/2018 | Hajela .................. A61F 2/1635 |
| 2019/0125523 A1 | 5/2019 | Barzilay |
| 2020/0157124 A1 | 5/2020 | Silvestrini |
| 2020/0345481 A1 | 11/2020 | Ellis |
| 2021/0100652 A1 | 4/2021 | Walz et al. |

\* cited by examiner

INTRAOCULAR LENSES WITH SHAPE-CHANGING OPTICS

CROSS-REFERENCE TO RELATED APPLICATIONS

The present application claims priority to U.S. Provisional Application No. 63/053,134 filed on Jul. 17, 2020 and incorporated by reference herein in its entirety.

TECHNICAL FIELD

The present disclosure relates to an accommodative intraocular lens that includes an optic that can change shape as the intraocular lens transitions from an accommodative state to a dis-accommodative state.

BACKGROUND

The lens of the eye constitutes cells arranged in a lamellar manner and is divided into a central nucleus and a peripheral cortex. The lens is enclosed by a cellular basement membrane (the lens capsule). Along with the cornea, the lens focuses light (refraction) onto the retina of the eye. Refractive power is measured in diopters. The lens contributes approximately a third of the refractive power of the eye and it is responsible for fine-tuning the eye's focus so that objects over a wide range of distances can be seen clearly. The process whereby the lens changes the focus of the eye is called accommodation. Accommodation is measured in diopters of accommodation change. Accommodation occurs with contraction of the ciliary muscle, which reduces force on the lens suspensory zonular fibers (zonules). The lens zonules extend from the ciliary muscle to the near equatorial regions of the lens and suspend the lens behind the iris. Reduction of force on the zonules allows the lens of the eye to assume its natural, less stressed, more spherical shape; thereby increasing it dioptric power, and this brings objects at near into focus. The change in focus from distance focus to near focus is generally smooth and controlled by a complex neural feedback mechanism. The relative contribution to accommodation of the lens zonules, the lens capsule, the lens nucleus and the surrounding lens cortex is the subject of ongoing research.

With age, there is a gradual reduction in the ability of the lens to alter the focus of the eye (presbyopia). This manifests in a gradual loss of capacity to focus on near objects, typically requiring optical assistance (e.g. reading glasses, bifocals) beginning around the fifth to sixth decades of life. There are many theories explaining accommodation and the loss of accommodation. It is generally accepted that with aging the lens substance itself becomes more resistant to deformational change (e.g. less pliable, more rigid, or firmer). A comprehensive and definitive understanding of accommodation and the cause(s) of presbyopia is still subject to scientific inquiry. However, much is already known regarding structural and functional changes of the lens and the other structures of the eye that contribute to accommodation and to the gradual loss of accommodation.

The ciliary muscle has been shown to function throughout life without significant loss of function with aging. The lens zonules include anterior fibers which attach to the lens anterior to the lens equator, equatorial fibers which attach at the lens equator, and posterior fibers which attach posterior to the lens equator. It has been demonstrated that the anterior fibers primarily alter the shape of the anterior lens surface and the posterior fibers primarily control the shape of the posterior lens surface. The sparse and less robust equatorial fibers play a lesser role in changing of the shape of the surfaces of the lens. Some conditions and genetic disorders may contribute to lens zonule loss or breakage, but in general the lens zonules remain functional throughout life. Therefore, changes in the lens zonules are not considered a significant factor in the loss of accommodation.

The lens nucleus and cortex are unique in that the cellular makeup and structure of the lens allows for reshaping of individual cells with intracellular flow of cytosol (the fluid within the cell). As a result, the individual cell shape can change and cumulatively the entire lens contents, contained within the lens capsule, can be considered a viscoelastic or "semi-flowable fluid". However, in youth, the lens nucleus is less resistant to deformational change (e.g. less firm or more pliable), than compared to the lens cortex. This is termed the lens elastic gradient. Studies have shown that with aging the lens nucleus becomes more resistant to deformational change (e.g. less pliable, or firmer). Likewise, studies show that the lens cortex also becomes more resistant to deformational change (e.g. less pliable or firmer with aging). However, the lens nucleus becomes firmer at a faster rate than the lens cortex. The crossover, where the nucleus becomes firmer, less pliable, or more resistant to deformational change than the lens cortex occurs around age 40-50 years of age. This relative change in the difference in firmness of the nucleus relative to that of the cortex correlates with the loss of accommodation and the onset of presbyopia.

The human crystalline lens can be affected by one or more disorders or conditions that reduces its function and/or reduces the clarity of the lens. A common condition that occurs with aging is the gradual opacification and reduced transparency of the lens of the eye. This condition is termed a cataract. Surgical removal of a cataractous lens and placement of an artificial replacement lens (such as an intraocular lens ("IOL")) within the eye is a common surgical procedure. The development of a suitable IOL that can provide the optical quality and accommodation provided by the youthful biological lens has not been developed.

There are generally two classes of IOLs that have been developed that attempt to overcome the lack of accommodation of an IOL used to replace the natural lens when cataract surgery is performed: pseudo-accommodating lenses and accommodating lenses. A pseudo-accommodating lens can be a multiple focal point lens that uses a ring for distance focus and one or more center optics for intermediate and near focus. Other designs use diffraction optics to obtain a range of focus or use optics to achieve an extended depth of focus (EDOF). Multi-focus optics, diffraction optics, and EDOF optic IOLs can result in disruptive optical aberrations such as glare, halos, reduced contrast sensitivity, etc. Centration of these lenses within the capsular bag is important to their best visual function. These lenses use non-deforming optical elements and do not achieve the visual quality of a natural, youthful lens of the human eye. The accommodating class of IOLs includes a silicone elastomeric hinged lens that allows forward movement, of the optic when the eye focuses at near. These lenses are typically placed in the lens capsular bag (the remaining thin layer of basement membrane that is the outermost layer of the natural lens and is typically left in place when the contents of the lens are removed during cataract surgery). Due to progressive fibrosis and stiffening of the lens capsule following cataract removal, the effective accommodation with these lenses is known to diminish over time.

Overall, these lenses may be adequate for distance and intermediate vision, but only provide accommodation of about two diopters at most and this value has been shown to diminish over time.

Shaped haptics, levers, or other mechanical elements have been described to translate the compressive force exerted by the elasticity of the lens capsule and/or the radial compressive force exerted by the ciliary muscles to affect desired axial displacement of the IOL optic along the optical axis. Additional examples may also provide flexible hinge regions of the haptic to facilitate axial displacement of an IOL along the optical axis. Several examples include annular ring elements in contact with the lens capsule and that use the axial compression of applied force by the capsule to effect axial displacement of the IOL optic along the optical axis. However, these IOLs are configured to be generally of fixed optical power and in line with the optical axis of the eye. As such, the axial displacement of the optical elements of these IOLs that is possible limits the dioptric power change attained. Some single or multiple optic lenses have incorporated a shape changing and axial displacement changing combination of lenses, such as a shape changing optic coupled to zonular contact haptics whereby axial compression of the lens capsule during accommodation results in both anterior displacement of the flexible optic, as well as compression of the sides of the optic. Other described IOLs rely on a posterior flexible region separated from a flexible anterior lens by an articulating member about the circumference.

It is known that the lens capsule, following cataract surgery, becomes less pliable and more fibrotic. IOLs that rely on retained capsular elasticity/pliability are unlikely to retain accommodating/dis-accommodating ability.

Surface shape changing lenses are more likely to result in greater degrees of dioptric power change. These lenses include lenses with fluid filled chambers that rely on axial compression by the lens capsule to force fluid from one chamber into a central lens and thereby change the shape and therefore the optical surface power of the lens. Other lenses use the compressive force by the lens capsule to provide a compressive force about the equatorial periphery of a flexible lens to shape change the lens. These are generally two-part systems with a circumferential haptic design with a central fixed posterior lens that fits within the capsule and then a separately placed pliable optic secured within the outer haptic ring. Compression by the "elastic" lens capsule is meant to provide an axial compressive force to the central lens flexible optic along the optical axis. Other IOLs use a compressive force exerted on rigid haptics to compress a pliable optic against a separate fixed power posterior lens. These IOLs rely on the shape change of the posterior surface of the pliable optical element pressed against a fixed optical element or pressed against a relatively rigid posterior lens capsule to alter the dioptric power of the lens system. Other IOLs incorporate a skirt with a capsular contact ring. Such IOLs rely on axial compression exerted by the "elastic" lens capsule to impart a compressive force on a capsular contact ring and the mechanical design of this ring pulls radially about the equator of the IOL's flexible optic. Again, because these IOLs rely on retained capsular elasticity/pliability and because it is generally known that the lens capsule following cataract surgery becomes less pliable and more fibrotic, it is unlikely these lenses will retain accommodating/dis-accommodating ability. None of the shape changing accommodating IOLs described above mimic the natural human lens during accommodation or effectively account for the inevitable loss of capsular elasticity/pliability and progressive fibrosis and stiffening of the lens capsule.

SUMMARY

The present disclosure relates to ophthalmic devices including IOLs and more particularly to accommodating intraocular lenses (accommodating IOLs). In an aspect, an IOL can comprise a shape-changing optic. The IOL can be configured to assume an accommodated state, a dis-accommodated state, and states therebetween. The IOL can comprise an elastic anterior face located anterior to the equator, having an anterior surface and a posterior surface, and having a periphery. The IOL can also include a posterior face having an anterior surface, a posterior surface, and a periphery. The IOL can further include an elastic side wall extending across the equator and extending from the anterior face to the posterior face. The IOL additionally can include a chamber containing material that is located between the anterior face and the posterior face. The IOL can also include at least one haptic having a medial portion and a lateral portion. The medial portion can extend (directly or indirectly) from the periphery of the anterior face, the periphery of the posterior face, or both. The anterior face can be more resistant to deformational change than the material contained within the chamber.

In another aspect an IOL has an optical axis extending in an anterior-posterior direction and an equator extending in a plane substantially perpendicular to the optical axis. The IOL can comprise an elastic anterior face located anterior to the equator, and a posterior face located posterior to the equator. The anterior face, the posterior face, or both can comprise a poly(dimethylsiloxane) elastomer having a durometer between about 30 Shore A to about 50 Shore A. A chamber can be located between the anterior face and the posterior face and can comprise a silicone oil comprising polysiloxanes comprising diphenyl siloxane and dimethyl siloxane units. The silicone oil has a maximum viscosity of about 700 mm$^2$/s at 25° C. and has a mean molecular weight of less than about 3000 Daltons.

In another aspect, an IOL has an optical axis extending in an anterior-posterior direction and an equator extending in a plane substantially perpendicular to the optical axis. The IOL can comprise an elastic anterior face located anterior to the equator and a posterior face located posterior to the equator. The anterior face, the posterior face, or both can comprise a polysiloxane that is at least 99% poly(dimethylsiloxane) elastomer. The IOL can further include a chamber located between the anterior face and the posterior face and can comprise a silicone oil comprising polysiloxanes comprising diphenyl siloxane and dimethyl siloxane units.

DETAILED DESCRIPTION

The present disclosure relates to an IOL such as, for example, an accommodative IOL. As used herein with respect to a described element, the terms "a," "an," and "the" include at least one or more of the described element(s) including combinations thereof unless otherwise indicated. Further, the terms "or" and "and" refer to "and/or" and combinations thereof unless otherwise indicated. By "substantially" is meant that the shape or configuration of the described element need not have the mathematically exact described shape or configuration of the described element but can have a shape or configuration that is recognizable by one skilled in the art as generally or approximately having the described shape or configuration of the described element. As used herein, the terms "anterior," "posterior," "superior," "inferior," "lateral," and "medial" refer to the position of elements when a patient is in a standard anatomical position unless otherwise indicated. The terms "left," "right," "top" and "bottom" refer to the position of elements as they are depicted in the drawings and the terms "left" and "right" can be interchanged unless indicated otherwise. The terms "first," "second," etc. are used to distinguish one element from another and not used in a quantitative sense unless indicated otherwise. Thus, a "first" element described below could also be termed a "second" element. A component operably coupled to another component can have intervening components between the components so long as the IOL can perform the stated purpose. By "integral" or "integrated" is meant that the described components are fabricated as one piece or multiple pieces affixed during manufacturing or the described components are otherwise not separable using a normal amount of force without damaging the integrity (i.e. tearing) of either of the components. A normal amount of force is the amount of force a user would use to remove a component meant to be separated from another component without damaging either component. As used herein a "patient" includes a mammal such as a human being. Mole % as used herein refers to the average percentage of the siloxane units of a particular composition (e.g. in a polysiloxane molecule). As used herein, the term "about," when referring to a value or range is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate for the IOL to perform its desired functionality.

All IOLs as described herein are used for medical purposes and are therefore sterile. Components of IOLs as described herein can be used with IOLs described herein as well as other IOLs. For example, an IOL as described herein can be placed anterior to an existing, previously placed IOL. IOLs include fixed power, multifocal, EDOF, diffractive and other variable focus lenses. Although the drawings show certain elements of an IOL in combination, it should be noted that such elements can be included in other embodiments or aspects illustrated in other drawings or otherwise described in the specification. In other words, each of the disclosed aspects and embodiments of the present disclosure may be considered individually or in combination with other aspects and embodiments of the disclosure including patent applications incorporated by reference herein.

Unlike shape changing accommodating IOLs described by way of background, IOLs are provided herein that can mimic the gradient elastic properties of a natural youthful human lens during accommodation and include a shape-changing optic where components of the optic change shape as the IOL transitions from an accommodated state to a dis-accommodated state and vice versa. Without wishing to be bound by a specific mechanism of action, it is considered by some that the lens capsules' "elasticity" controls and shapes the lens as a whole (the lens nucleus and cortex). On this basis, the lens contents are considered pliable. However, the volume of the lens contents compared to the thickness and known modulus of elasticity of the lens capsule predicts that the lens capsule cannot solely control and alter the shape of the lens nucleus and cortex. Finite element analysis (FEA) predicts that radial tension about the equatorial region of a lens capsule filled with a soft pliable solid or liquid does not result in significant shape change to either the anterior or posterior surface of the lens compared to what is known to occur with the natural youthful human lens. Providing radial tension directed specifically to at least the anterior face of an accommodating IOL; having that tension directed at points anterior to the equator of the IOL; the anterior face of the IOL being more resistant to deformational change than the content(s) of a chamber underlying the anterior face; the anterior face demonstrating elastic properties in so much as the anterior face deforms when a force is applied to the anterior face and the anterior face will return to its original shape with the removal of the force, results in a greater amount of anterior face shape change and therefore accommodating dioptric power change than can be achieved with a similar force applied at points at or more near the equator of the IOL (e.g. equatorial). In addition, a force applied to the anterior face at points anterior to the equator of the IOL requires less diameter change of the anterior face per diopter of power change of the IOL compared to a similar force applied at points at or more near the equator of the IOL thereby allowing the anterior face of the IOL to shape change even with very small amounts of anterior face diameter change when going from an accommodated state, a dis-accommodated state, and states in between.

In particular, in an aspect, an IOL comprising a shape changing optic that can assume an accommodated state, a dis-accommodated state, and states therebetween is provided. Components of the shape-changing optic can be deformable such that ocular compression force or tensile force applied to the optic caused by ciliary muscle contraction or relaxation causes one or more components of the optic to change shape and allows the optic to change dioptric power. As such, components of a shape-changing optic can deform or change shape when a force is applied. If a component is less resistant to deformational change than another component, the former component is more likely to, or to a greater degree, deform for a given amount of applied or removed force than the latter component. A component is more resistant to deformational change than another component, if the former component is less likely to, or to a lesser degree, deform for a given amount of applied or removed force than the latter component. It is understood that for any given component resistant to deformational change, the force applied/removed to such component does not exceed the force that results in breakage of the component such that it is no longer useful for its therapeutic purpose.

Figure 1:
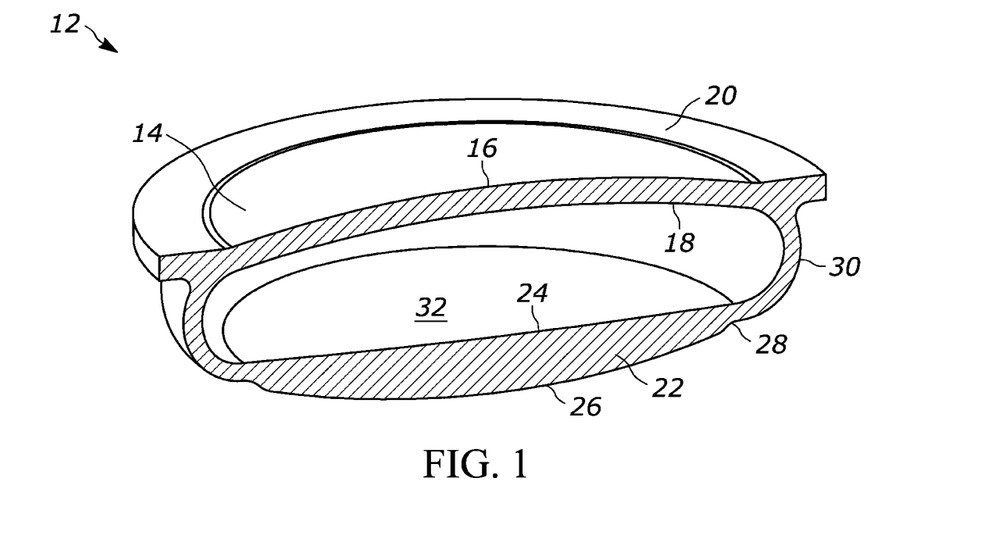
FIG. 1 is a perspective cross-sectional view of a shape-changing optic of an IOL according to an aspect of the present disclosure.
Figure 2:
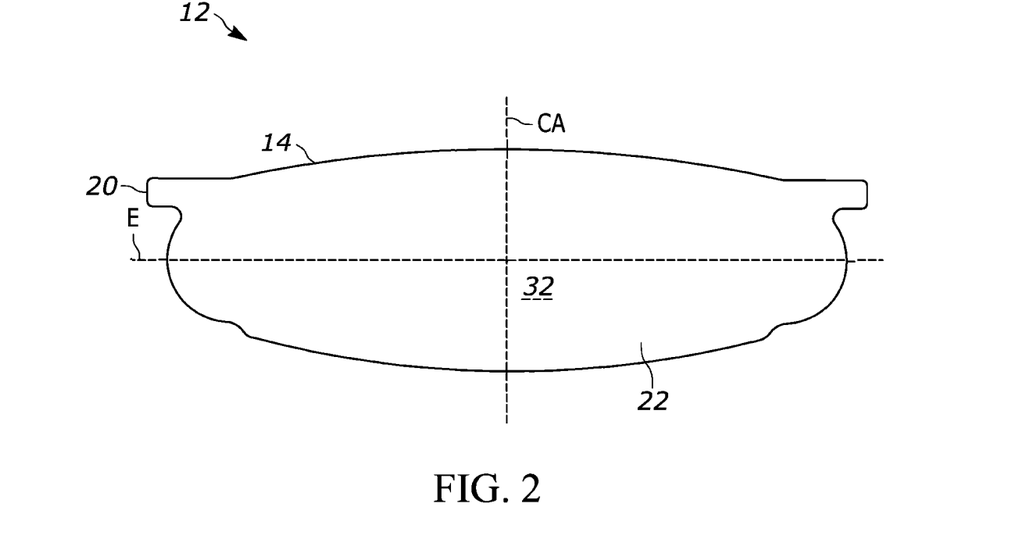
FIG. 2 is a side view of a shape-changing optic of an IOL according to an aspect of the present disclosure.
Figure 3:
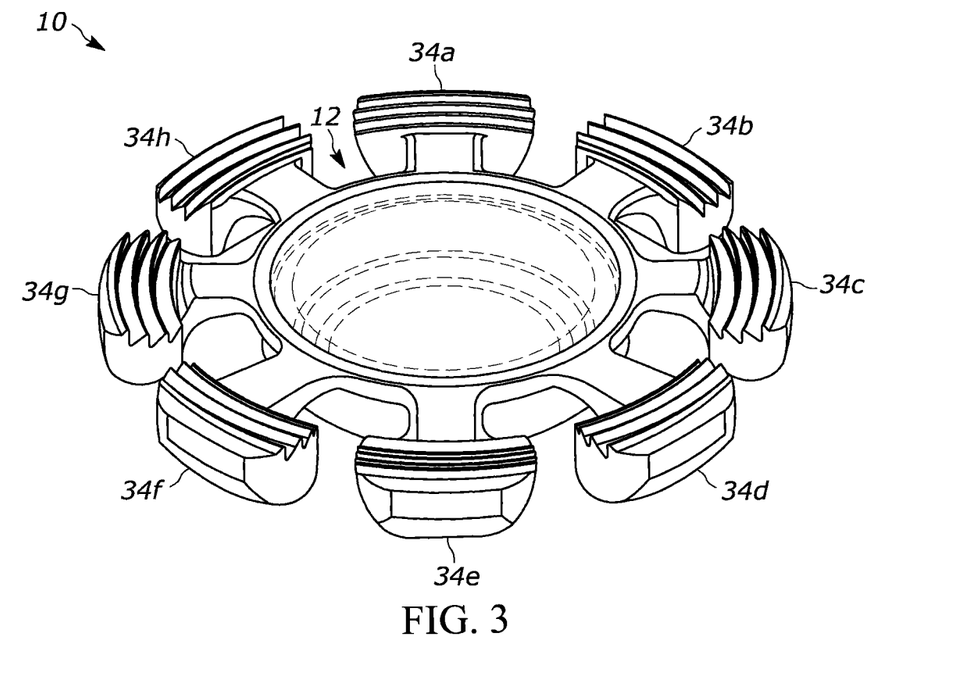
FIG. 3 is a perspective view of the IOL including the shape changing optic of FIGS. 2 and 3 including a depiction of haptics according to an aspect of the present disclosure.

FIG. 2 depicts a central or optical axis CA extending in an anterior-posterior direction and an equator E extending in a plane substantially perpendicular to the central axis. The equator is an imaginary line drawn around the circumference of a lens perpendicular to the optical axis, equally distant from the anterior face of the lens and the posterior face of the lens, dividing the lens into an anterior half and a posterior half. Referring to FIGS. 1-3, a shape-changing optic 12 of an IOL 10 can comprise an elastic anterior face 14 located anterior to equator E. Anterior face 14 can have an anterior surface 16, a posterior surface 18 and a periphery 20. Shape-changing optic 12 can also comprise a posterior face 22 having an anterior surface 24, a posterior surface 26, and a periphery 28. Shape-changing optic 12 can further include an elastic side wall 30 extending across equator E and extending from anterior face 14 to posterior face 22. A chamber 32 can be located between anterior face 14 and posterior face 22 and can house material or contents as described in more detail below. Components of the shape-changing optic can be made to be more or less resistant to deformational change by altering the thickness of the component, the type of material from which the component is fabricated, or by altering the chemical/material properties of the component material itself for example. With reference to FIG. 3, IOL 10 can further comprise at least one haptic 34 extending from the periphery of the anterior face. At least one haptic can also extend from the periphery of the posterior face, or the periphery of both the anterior face and the posterior face as described below.

Regarding specific components of an IOL, the anterior face, as stated above, can have elastic properties. Elastic properties can allow for the anterior face to change shape with an applied force, but also to return to its original configuration when the force is removed. It is beneficial that the anterior face be more resistant to deformational change (e.g. less pliable, firmer) than the contents or material contained within the chamber because when an outward radial force is applied to the anterior face, the contents of the chamber can more easily deform to allow flattening of the anterior face. Exemplary fabrication materials for the anterior face include silicone, an acrylic (hydrophobic or hydrophilic) polymer, polymethylmethalcryalate (PMMA), silastic, collamer, a suitable optical thermoplastic polymer, another suitable optical material, and suitable combinations thereof.

Figure 4:
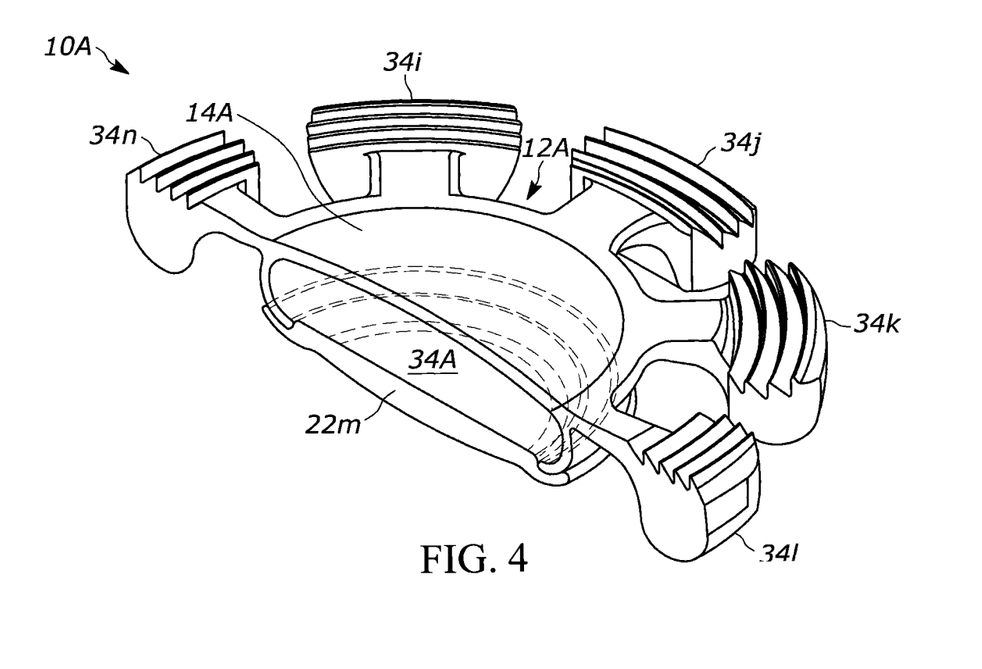
FIG. 4 is a perspective cross-sectional view of an IOL according to another aspect of the present disclosure.
Figure 5:
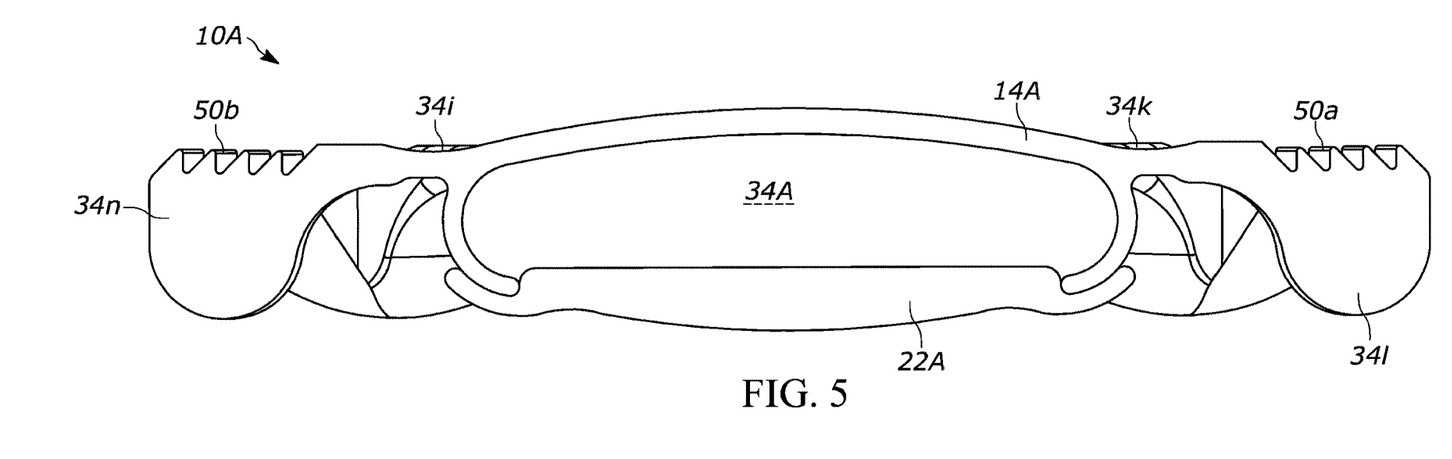
FIG. 5 is a side view of an IOL according to an aspect of the present disclosure.
Figure 6:
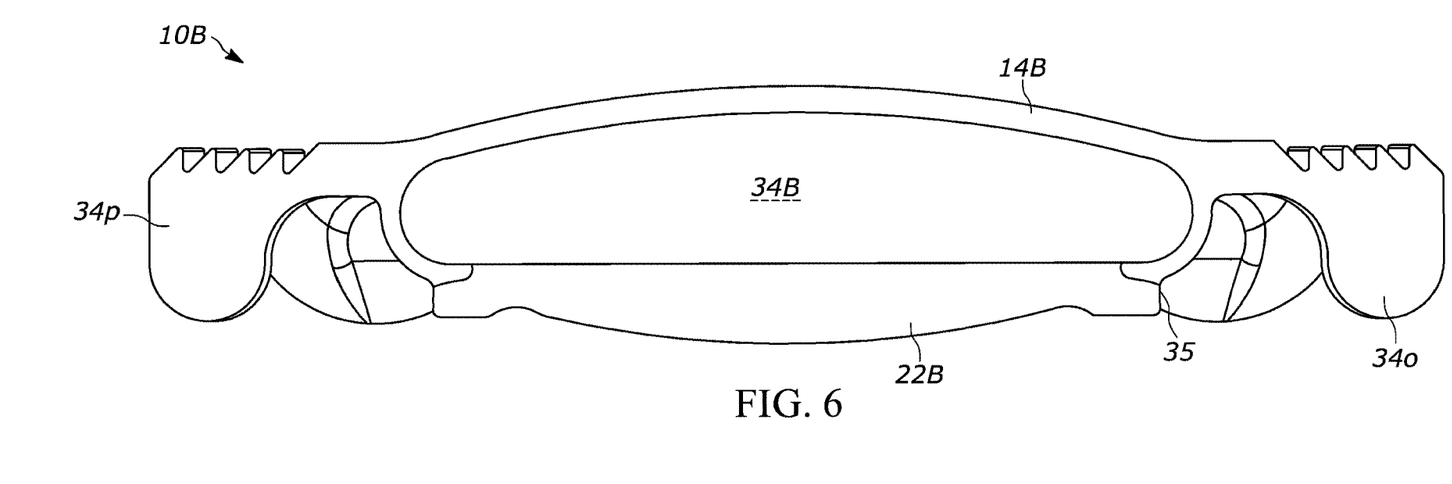
FIG. 6 is a side view of an IOL according to another aspect of the present disclosure.

Regarding the posterior face of the shape-changing optic, the posterior face can be more resistant to deformational change than the anterior face or the contents contained within the chamber of the shape-changing optic. The posterior face need not have the ability to change shape. When implanted and in certain aspects, the posterior face can rest against the posterior capsule and the vitreous substance and it may not be desirable to have those less predictable forces altering the power of the optic. Further, having a posterior face that is more resistant to deformational change than the anterior face or the contents of the chamber of the shape-changing optic can allow the posterior face optic to have a relatively more fixed power posterior lens permitting the incorporation of beneficial optical properties. In addition, a posterior face more resistant to deformational change can allow the contents of the chamber to reshape the side wall(s) when the anterior face changes shape in response to a force. The posterior face can be part of a one-piece integral IOL 10 as depicted in FIG. 1-3 or can be a two-piece integral IOL 10A as illustrated in FIG. 4-6. In certain aspects, the posterior face is elastic. Exemplary fabrication materials for the posterior face include silicone, an acrylic (hydrophobic or hydrophilic) polymer, polymethylmethalcryalate (PMMA), silastic, collamer, a suitable optical thermoplastic polymer, another suitable optical material, or suitable combinations thereof. The posterior face can comprise a lens with a variety of optical properties, such as, for example, a spherical, aspheric, toric, toroidal, multifocal, diffractive, extended depth of focus, or combinations thereof. As illustrated in FIG. 6, an IOL 10B can comprise a shape-changing optic where the posterior face 22B has a squared peripheral edge 35 to reduce posterior capsular opacification, by inhibiting, for example, peripheral lens epithelial cells from migrating across the posterior face.

Figure 7:
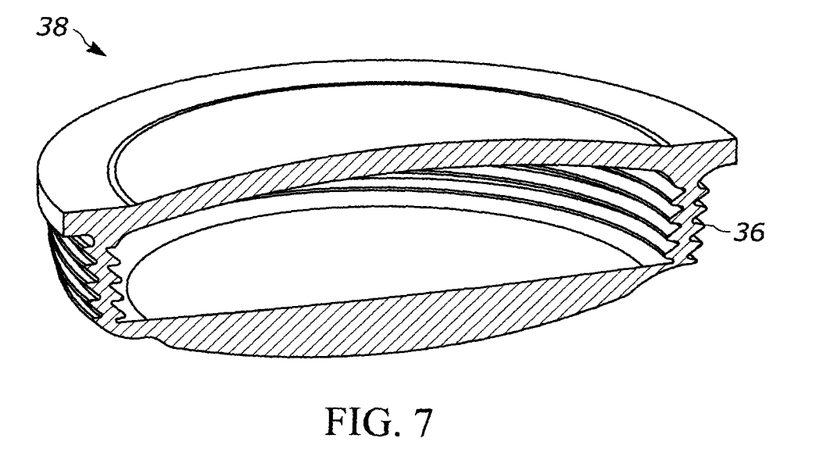
FIG. 7 is a perspective cross-sectional view of a shape-changing optic of an IOL according to an aspect of the present disclosure.
Figure 8:
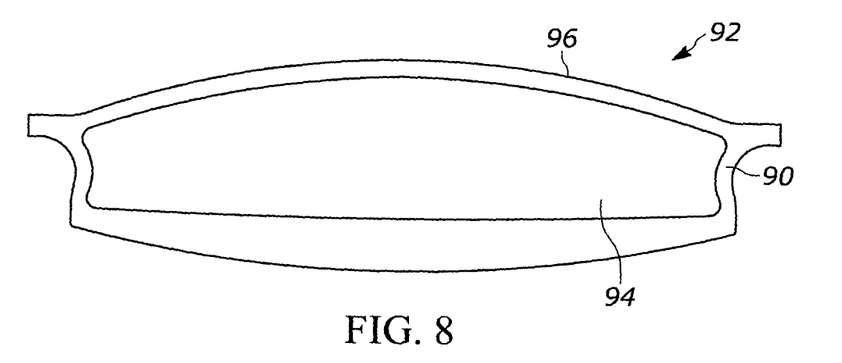
FIG. 8 is a side cross-sectional view of a shape-changing optic of an IOL according to an aspect of the present disclosure.

Regarding the side wall, as stated above, the side wall can have elastic properties. In certain aspects, the side wall can be fabricated from a material that is equal to or less resistant to deformational change than the anterior face. Such features can allow for the contents contained within the chamber to expand the area of the side wall to allow the volume of the contents of the chamber to remain the same when the anterior surface is flattened. Having the side wall deform can facilitate and allow for a greater amount of shape change to the anterior face of the shape-changing optic. Exemplary fabrication materials for the side wall include silicone, an acrylic (hydrophobic or hydrophilic) polymer, polymethylmethalcryalate (PMMA), silastic, collamer, a suitable optical thermoplastic polymer, another suitable material, or a suitable combination thereof. The side wall can also be equal to or less resistant to deformational change than the anterior face or the posterior face by being thinner than the anterior face or the posterior face. Alternatively, or in addition, the side wall 36 of a shape-changing optic 38 can be equal to or less resistant to deformational change by having a bellowed configuration as illustrated in FIG. 7. The bellows can be horizontally or vertically oriented or have other orientations to allow for peripheral side wall expansion or contraction. As illustrated in FIG. 8, the side wall 90 of a shape changing optic 92 can have a plano, concave, convex, or other configuration to facilitate displacement of the contents of chamber 94 against side wall 90 when anterior face 96 is flattened.

Figure 9:
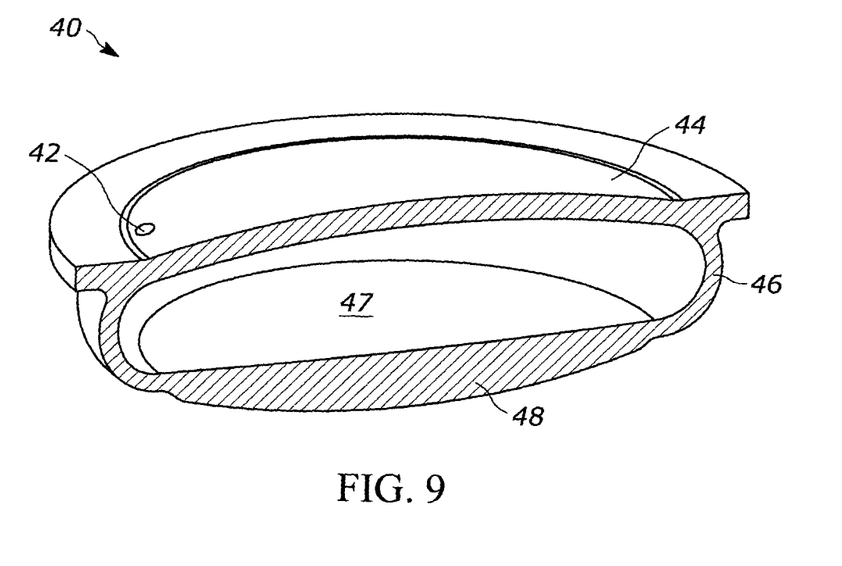
FIG. 9 is a is a side cross-sectional view of a shape-changing optic of an IOL according to an aspect of the present disclosure

Regarding the chamber, the chamber can be defined by the posterior surface of the anterior face, the anterior surface of the posterior face, and an inner surface of the side wall. The interior contents or material of the chamber can comprise a soft solid, a gel, a viscoelastic material, a flowable fluid, or a gas, or other suitable material. Exemplary materials that can be contained within the interior of the chamber include a soft silicone, or other soft material subject to deformational change, air or other gas, silicone oil (of various refractive indices), an aqueous solution of saline or hyaluronic acid, a viscoelastic polymer, polyphenyl ether, or other optical fluid, solid or gases, or suitable combinations thereof. The chamber can have an internal layer or coating to seal the contents of the chamber from the anterior face, the side wall and/or the posterior face. The chamber can be pre-loaded (e.g. by a manufacturer) with a suitable material. Alternatively, the chamber can be loaded with a suitable material by a clinician. For example, and with reference to FIG. 9, a shape-changing optic 40 of an IOL can define at least one port 42 (enlarged in FIG. 9 for purposes of clarity) sized and dimensioned to receive a needle or catheter, the needle or catheter being sized and dimensioned to deliver a fluid, gel, or gas to the chamber and/or to exchange fluid with a different material or a material having a different refractive index, for example. Although FIG. 9 illustrates the port defined by anterior face 44, the port can be defined by the side wall 46 or the posterior face 48 of the shape-changing optic. Having a port can allow a user to add or remove substance from chamber 47 to adjust the optical power of the lens. For example, by adding additional substance to the chamber, the volume of the substance can increase in the chamber resulting in an increase in the surface(s) curvature and the overall power of the lens and removing substance can decrease the volume of the substance in the chamber resulting in a decrease in the surface(s) curvature and the overall power of the lens. Also, by exchanging the substance for one with a different refractive index, the overall dioptric power and the range of accommodation of the IOL can be increased or decreased.

Regarding the at least one haptic of the IOL, such a haptic(s) is the portion of the IOL that is configured to interact with the lens capsule, the lens zonules, the ciliary muscle, or other parts of a patient's eye. The at least one haptic can be molded, shaped into, integral with, or otherwise extend from the shape-changing optic of an IOL. As illustrated in FIG. 3, the at least one haptic can comprise a plurality of haptics disposed about the circumference of the anterior face of the shape-changing optic. The at least one haptic can be elastic but can be more resistant to deformational change than the anterior face. An advantage to this is that the haptic can be firmer to provide a linear force from the haptic to the periphery of the anterior face. Without wishing to be bound by any particular mechanism of action, if the haptic were to be less resistant to deformational change than the anterior face, the radial tension could result in stretching of the haptic and less tension on the periphery of the anterior face. Thus, the anterior face may not shape change as much for a given force applied to the haptic. Exemplary fabrication materials for the at least one haptic include silicone, an acrylic (hydrophobic or hydrophilic) polymer, polymethylmethalcryalate (PMMA), silastic, collamer, a suitable optical thermoplastic polymer, another suitable material, or suitable combinations thereof.

Regarding the haptics, in certain aspects, each of the plurality of haptics is non-rotatable in response to axial compression along the optical axis on the shape-changing optic. In certain aspects, each of the haptics has a peripheral portion having a posterior face and an anterior face, with the posterior face being curved. In other aspects, the medial portion of each of the plurality of haptics medial portion extends from and is connected to the periphery of the anterior face such that the plurality of haptics changes the shape of the anterior face via application of radial force to the periphery of the anterior face in a direction perpendicular to the optical axis and not via axial compressive forces along the optical axis on the shape-changing optic or via axial compressive forces on the haptics.

FIGS. 3 to 6 illustrate an IOL where at least one haptic extends from the anterior face of a shape-changing optic. The shape-changing optic can change shape in response to an ocular force, specifically a force generated by the contraction or relaxation of the ciliary muscle of the patient's eye. The at least one haptic, interacting with the lens capsule, can apply radial outward tension to the anterior face when the ciliary muscle relaxes and radial outward tension is placed on the lens capsule via the lens zonules. The at least one haptic can be elastic but can be equal to or more resistant to deformational change than the anterior face.

Figure 10:
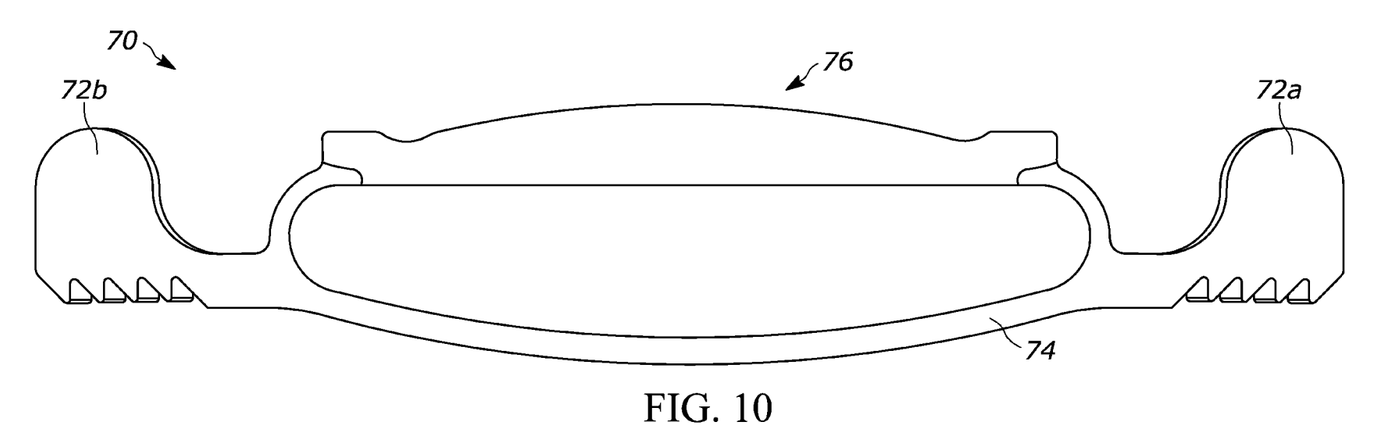
FIG. 10 is a side view of an IOL according to another aspect of the present disclosure.
Figure 11:
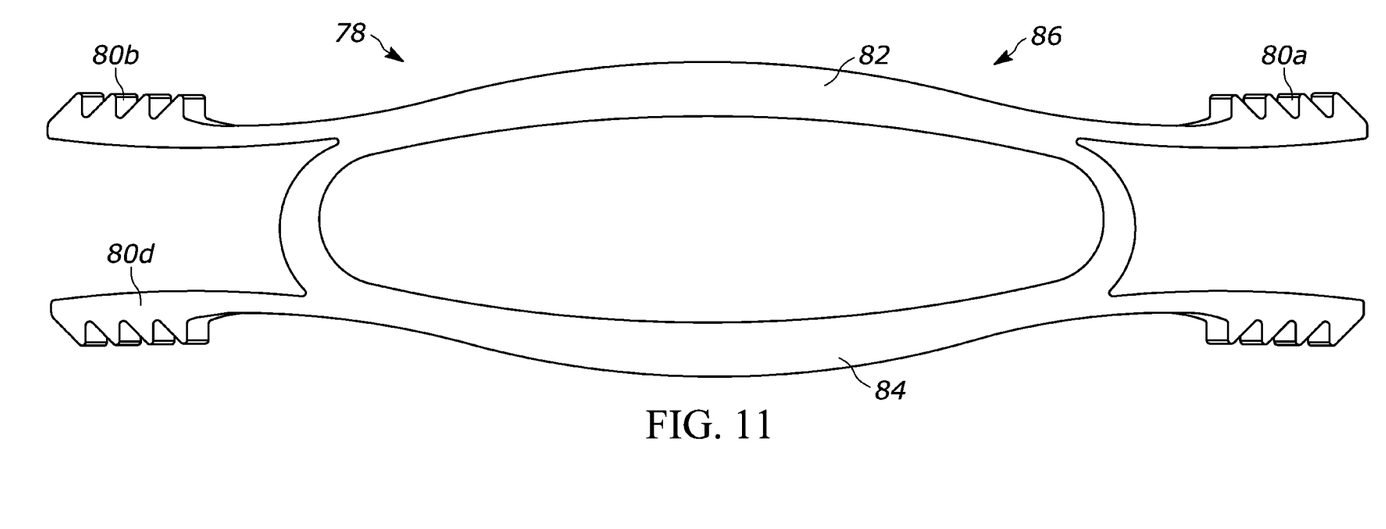
FIG. 11 is a side view of an IOL according to another aspect of the present disclosure.

FIG. 3 illustrates an aspect where a plurality of haptics extends circumferentially from the shape-changing optic. When implanted and when the ciliary muscles of a patient's eye relaxes (such as when the eye is in a dis-accommodated state), the ciliary muscles apply tensile force to the plurality of haptics (via the lens capsule with lens zonule attachments between the lens capsule and the ciliary muscles, for example). The plurality of haptics, in turn, can apply tensile force to the periphery of the anterior face at each site (referred to herein as an "extension site") where a haptic extends from the periphery of the anterior face. By having a plurality of haptics as depicted in FIGS. 3 and 4, the net result can be that the anterior face can be pulled outward from several extension sites (such as, for example, eight extension sites as illustrated in FIG. 3) and functionally result in relatively symmetric radial tension placed on the periphery of the anterior face of the shape-changing optic. Referring to FIG. 10, in certain aspects, an IOL 70 includes at least one haptic 72 extending from posterior face 74 of shape-changing optic 76. By having the force applied to the posterior face, a change in shape of the optic can be achieved independent of or in combination with a force applied to the anterior face. Referring to FIG. 11, in other aspects, an IOL 78 includes at least one haptic 80 extending from anterior face 82 and posterior face 84 of shape-changing optic 86. If a force is applied to both the posterior and the anterior faces, the total dioptric power change of the IOL for a given force can be increased. In other words, if a force is applied to both the anterior and posterior face, shape change can be obtained to both surfaces and thereby increase overall accommodation.

The at least one haptic can engage the inner surface of the lens capsule or the outer surface of the lens capsule. Referring to FIGS. 3-6, the peripheral portion of the at least one haptic 34 can comprises ridges 50 as illustrated in FIGS. 3-6 configured to engage an inner surface of a lens capsule. For example, ridges 50 can interact with the lens capsule to stabilize the haptics within the lens capsule. Ridges can also allow the haptics to interact and fixate into the lens capsule. Such an aspect can allow IOL placement within the capsular bag, while still allowing translation of tension/relaxation of the lens capsule (via the lens zonules and ciliary body) during accommodation/dis-accommodation of the lens. Current haptic designs do not allow the haptics to be positioned within the lens capsule while fixating the haptics to allow tension/relaxation on the lens capsule to translate forces into the haptics. Current haptic designs are smooth and allow the capsule and haptic to glide past each other, which does not allow the translation of forces placed on the peripheral lens capsule (via the zonules and ciliary muscle). When placing the IOL inside the capsular bag, the ridge(s) can be configured to allow the IOL to be rotated until the desired rotational position of the IOL is achieved. Once the IOL is rotated into its desired position, the forces on the haptics fixate lateral portions of the haptics to the inside peripheral edge of the lens capsule. The ridges then provide resistance to these forces and facilitate the forces from the ciliary body, zonules, and lens capsule into a force on the haptic(s).

Figure 12:
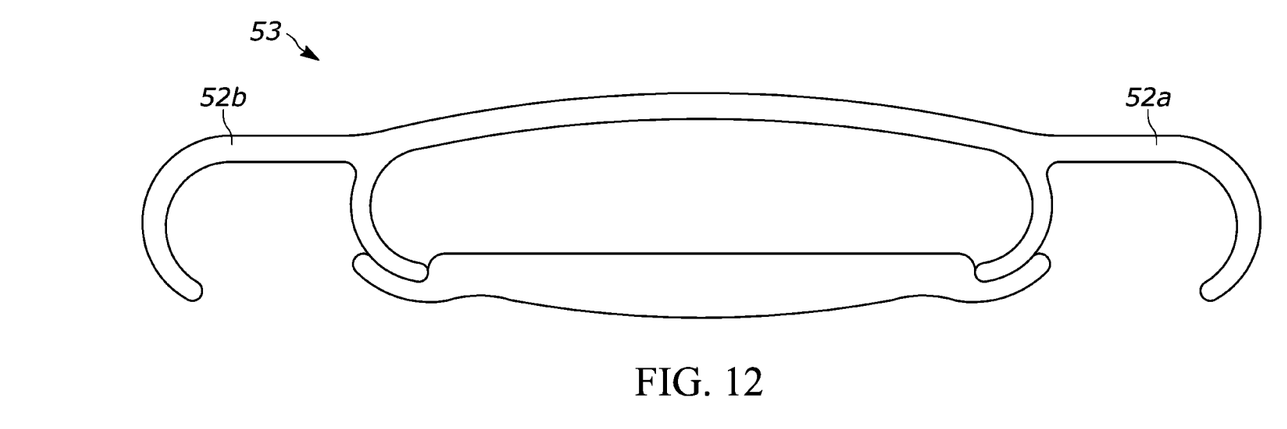
FIG. 12 is a side view of an IOL according to another aspect of the present disclosure.

Regarding the at least one haptic engaging the outer surface of the lens capsule, when an IOL is placed anterior to an existing, previously implanted IOL, or when placed anterior to the lens capsule, the at least one haptic can engage the outer surface of the lens capsule. Referring to FIG. 12, the peripheral portion of haptic 52 of an IOL 53 can comprise a hook-shaped/substantially J-shaped configuration to engage or curve around an outer surface of a lens capsule. The peripheral end of the peripheral portion can be an atraumatic end so that it does not damage zonules or the lens capsule. The at least one haptic (for example the right haptic and/or the left haptic) can each comprise a plurality of hooks. Hook or substantially J-shaped haptics can allow an IOL to use the force translated from the ciliary muscle to the lens capsule, via the lens zonules, without requiring placement of haptics against elements of the ciliary muscle. Such an embodiment can avoid known potential complications of haptics placed against the ciliary muscle, such as uveitis, glaucoma, and bleeding (e.g. hyphema). Such an embodiment can be implemented in patients that have an already implanted IOL or patients that do not have an already implanted IOL.

Figure 13:
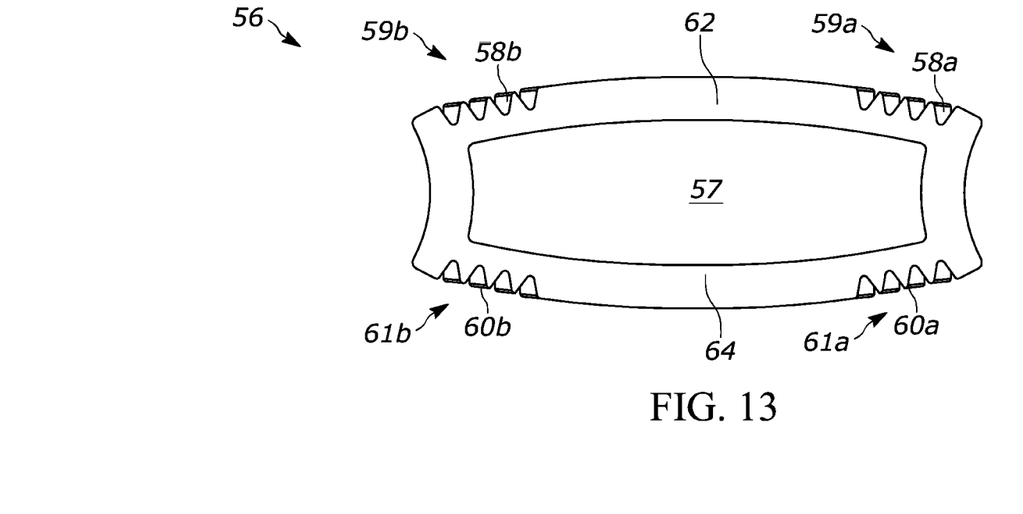
FIG. 13 is a side view of a shape-changing optic of an IOL according to an aspect of the present disclosure.

Referring to FIG. 13, the shape-changing optic itself can define ridges to engage the inner surface of a lens capsule. For example, the shape-changing optic 56 can include an expandable chamber 57, that has an integrated haptic with ridges 58 and 60 on periphery 59 of the anterior face 62 and/or the periphery 61 of the posterior face 64. When tension is placed on the lens capsule by the zonules (e.g. when the ciliary muscle relaxes), the force can be translated (by the ridges engaging the capsule) specifically to the anterior and posterior faces and not just translation of a general force to the entire lens. The anterior face, the posterior face, and/or the side walls can be more resistant to deformational change than the contents of the chamber. This configuration can allow forces from the lens capsule to provide radial tension to the haptics and thus to the anterior face, the anterior face being anterior to the equator of the lens; and/or to provide radial tension to the posterior face, the posterior face being posterior to the equator of the lens. The side walls can be configured to allow for the material in the chamber displaced by the flattening of the anterior face and/or the posterior face to expand into the area of the side wall, thereby allowing the volume of material within the chamber to remain the same.

Figure 14:
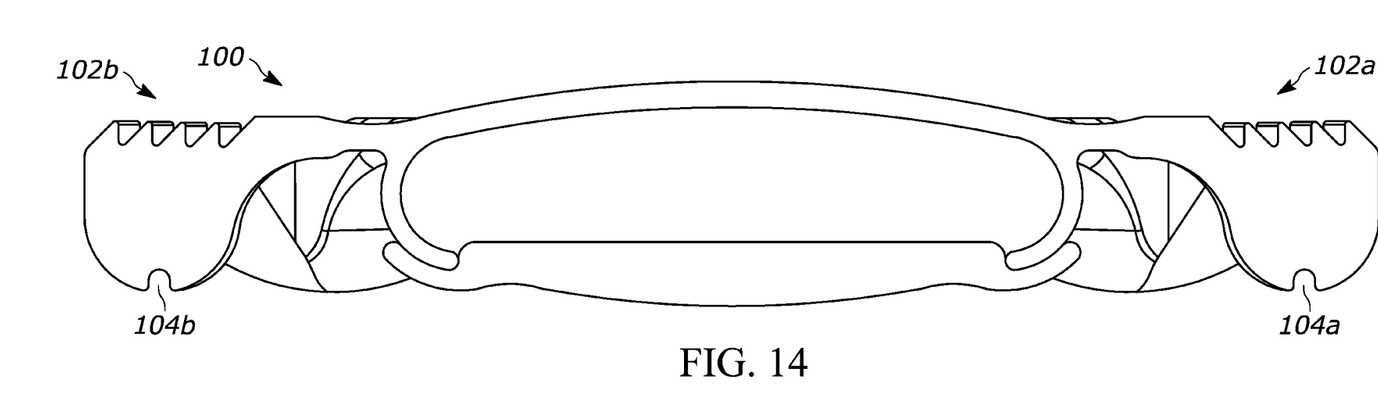
FIG. 14 is a side view of an IOL according to another aspect of the present disclosure.
Figure 15:
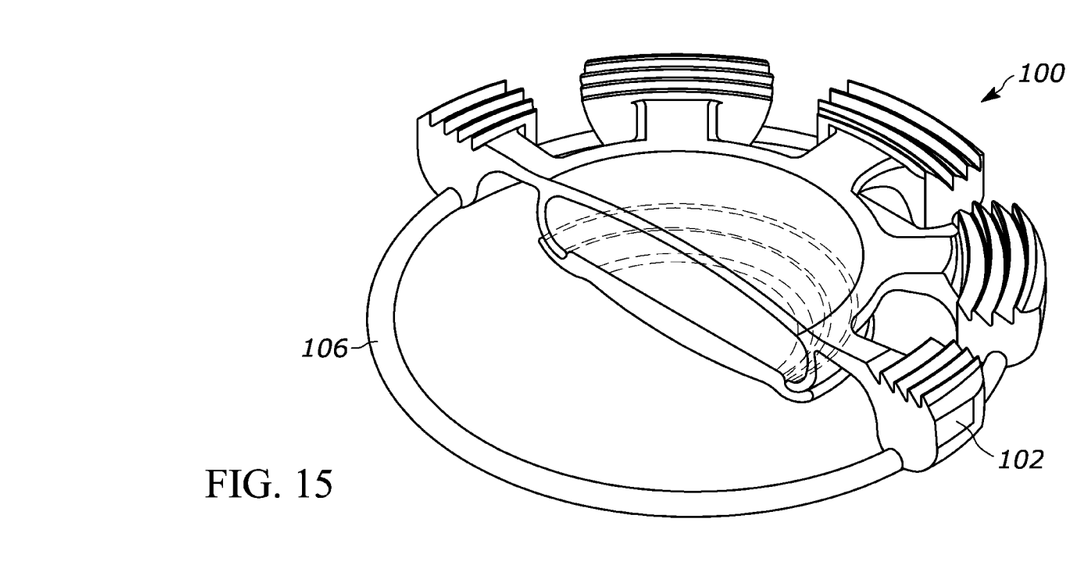
FIG. 15 is a perspective cross-sectional view of the IOL of FIG. 14 according to an aspect of the present disclosure.

Referring to FIGS. 14 and 15, in certain aspects, an IOL 100 is provided where the bottom of haptic 102 defines a recess 104. Such a recess can accommodate a stabilizing ring 106, for example, to keep the haptics from holding inwards with lens capsule fibrosis. Stabilizing ring can be fabricated from any of the materials described above with respect to the anterior and/or posterior faces of the shape changing optic.

In certain aspects, the present disclosure provides an IOL that has an optical axis extending in an anterior-posterior direction and an equator extending in a plane substantially perpendicular to the optical axis. The IOL can comprise an elastic anterior face located anterior to the equator and a posterior face located posterior to the equator. The anterior face, the posterior face, or both can comprise a poly(dimethylsiloxane) elastomer having a durometer between about 30 Shore A to about 50 Shore A. In certain embodiments, the durometer can be about 50 Shore A. The IOL can further include a chamber located between the anterior face and the posterior face and can comprises a silicone oil comprising polysiloxanes comprising diphenyl siloxane and dimethyl siloxane units. The polysiloxanes can comprise end blocking groups of trimethylsiloxane. The silicone oil can have a maximum viscosity of about 700 mm$^2$/s at 25° C., including a viscosity between about 500 mm$^2$/s at 25° C. to about 600 mm$^2$/s at 25° C. In certain embodiments, the silicone oil can have a mean molecular weight of less than about 3,000 Daltons. It should be noted that this described embodiment can include all the features and aspects described in all other embodiments and aspects of the present disclosure.

An IOL having such features has several advantages. By way of background, in a natural, healthy eye, a lens capsule deforms the lens cortex and lens nucleus (the lens contents) by virtue of the lens cells deforming. This is because the cytosol within each individual lens cell is free flowing and, in aggregate, the lens contents acts like a flowable fluid. Accordingly, the lower the viscosity of the fluid within the chamber of the IOL, the easier it is for the fluid to move in response to force applied by the anterior face and/or the posterior face of the IOL. As such, at least the anterior face comprising a poly(dimethylsiloxane) having a durometer between about 30 Shore A to about 50 Shore A in combination with a chamber containing a silicone oil having a maximum viscosity of about 700 mm$^2$/s at 25° C. and having a mean molecular weight of less than about 3,000 Daltons allows the anterior face to be more resistant to deformational change than the contents of the chamber underlying the anterior face, allows the anterior face to demonstrate elastic properties such as deforming when a force is applied to the anterior face and returning to its original shape when the force is removed resulting in an effective amount of anterior face shape change and therefore accommodating dioptric power change. Such an IOL more closely mimic the elastic gradient of a natural youthful human lens during accommodation particularly when radial tension is directed specifically to at least the anterior face and the tension is directed at points anterior to the equator of the IOL. Further, an anterior and/or posterior face comprising a poly(dimethylsiloxane) having a durometer between about 30 Shore A to about 60 Shore A has sufficient tear strength necessary to mold the lens during manufacturing. In certain embodiments, the IOL can include an elastic side wall extending across the equator and extending from the anterior face to the posterior face. The elastic side wall can also have a durometer between about 30 Shore A to about 50 Shore A, in addition to the anterior face and/or the posterior face having such a durometer value range.

In some embodiment's silicone oil is provided that includes smaller polymers having a mean molecular weight of less than about 3,000 Daltons, or between about 1,000 and about 3,000 Daltons. In general, the smaller molecular size of silicone oil polymers correlates with a lower viscosity of the silicone oil. Viscosity relates to the easy with which molecules in a fluid can move past each other, and smaller molecules having a lower molecular weight interact less, causing a decrease in viscosity. It is desirable to have a low viscosity of silicone oil in the fluid chamber of an accommodating IOL to allow a faster response time during accommodation/dis-accommodation. In some embodiments, the silicone oil has a mean molecular weight of less than about 2,500 Daltons. In further embodiments, the silicone oil has a mean molecular weight of less than about 2,000 Daltons. In further embodiments, the silicone oil is provided that has a mean molecular weight between about 1,500 and about 3,000 Daltons. In a yet further embodiment, the silicone oil has a mean molecular weight between about 2,000 and about 3,000 Daltons. In an additional embodiment, the silicone oil has a mean molecular weight between about 1,500 and about 2,500 Daltons. In a further embodiment, the silicone oil has a mean molecular weight from about 1,750 to about 2,750 Daltons. In a yet further embodiment, the silicone oil has a mean molecular weight from about 2,000 to about 2,500 Daltons. Higher molecular weight silicone oils can have a correspondingly high viscosity, which can reduce the response time of the accommodating IOL.

In certain aspects, the present disclosure provides an IOL that has an optical axis extending in an anterior-posterior direction and an equator extending in a plane substantially perpendicular to the optical axis. The IOL can comprise an elastic anterior face located anterior to the equator and a posterior face located posterior to the equator. The anterior face, the posterior face, or both can comprise a polysiloxane that is at least 99% poly(dimethylsiloxane) elastomer. In other words, the polysiloxane can have no phenyl units, trace amounts of phenyl units, or immeasurable amounts of phenyl units such that the IOL achieves its desired functionality as described herein. The IOL can further comprises a chamber located between the anterior face and the posterior face. The chamber can comprise a silicone oil comprising polysiloxanes comprising diphenyl siloxane and dimethyl siloxane units. In certain embodiments, the polysiloxanes comprise at least about 30 mole % diphenyl siloxane as polymer chains without phenyl groups can absorb into the poly(dimethylsiloxane). It should be noted that this described embodiment can include all the features and aspects described in all other embodiments and aspects of the present disclosure. An anterior and/or posterior face comprising polysiloxane that is at least 99% poly(dimethylsiloxane) minimizes absorption of the silicone oil into anterior and/or posterior face. This is important as absorption of the silicone oil into the anterior and/or posterior face can change the mechanical properties of the anterior and/or posterior face. In certain embodiments, the IOL can further comprise an elastic side wall extending across the equator and extending from the anterior face to the posterior face wherein the elastic side wall also comprises a polysiloxane that is at least 99% poly(dimethylsiloxane), in addition to the posterior face and/or anterior face have this 99% poly(dimethylsiloxane).

Each of the disclosed aspects and embodiments of the present disclosure may be considered individually or in combination with other aspects and embodiments as well as with respect to other intra-ocular lenses, such as IOLs disclosed in U.S. patent application Ser. No. 16/288,723 filed on Feb. 28, 2019 and incorporated by reference in its entirety and U.S. Provisional Application No. 62/842,788 filed on May 3, 2019 and incorporated by reference in its entirety. In addition, orientations of a shape-changing optic can be modified. For example, when implanted, the lens can be flipped such that the anterior face is facing in a posterior direction and the posterior face is facing in an anterior direction. Further, the IOL can be configured such that it is foldable for insertion. Further, while certain features of embodiments may be shown in only certain figures, such features can be incorporated into or deleted from other embodiments shown in other figures or otherwise disclosed in the specification. Additionally, when describing a range, all points within that range are included in this disclosure.

What is claimed is:

1. An intraocular lens (IOL) having an optical axis extending in an anterior-posterior direction and an equator extending in a plane substantially perpendicular to the optical axis, the IOL comprising:
   an elastic anterior face located anterior to the equator;
   a posterior face located posterior to the equator, wherein the anterior face, the posterior face, or both comprises a poly(dimethylsiloxane) elastomer having a durometer between about 30 Shore A to about 50 Shore A; and
   a chamber located between the anterior face and the posterior face and comprising a silicone oil comprising polysiloxanes comprising diphenyl siloxane and dimethyl siloxane units, the silicone oil having a maximum viscosity of about 700 mm$^2$/s at 25° C. and having a mean molecular weight of less than about 3000 Daltons.

2. The IOL of claim 1, wherein the polysiloxanes comprise end blocking groups of trimethylsiloxane.

3. The IOL of claim 1, wherein poly(dimethylsiloxane) elastomer has a durometer of about 50 Shore A.

4. The IOL of claim 1, wherein the silicone oil has a viscosity between about 500 mm$^2$/s at 25° C. to about 700 mm$^2$/s at 25° C.

5. The IOL of claim 1, wherein the silicone oil has a mean molecular weight of between about 1,000 Daltons to about 3,000 Daltons.

6. The IOL of claim 1, further comprising an elastic side wall extending across the equator and extending from the anterior face to the posterior face.

7. The IOL of claim 1, further comprising a plurality of haptics connected to a periphery of the anterior face, each of the plurality of haptics being non-rotatable in response to axial compression along the optical axis of the IOL.

8. An intraocular lens (IOL) having an optical axis extending in an anterior-posterior direction and an equator extending in a plane substantially perpendicular to the optical axis, the IOL comprising:
   an elastic anterior face located anterior to the equator;
   a posterior face located posterior to the equator, wherein the anterior face, the posterior face, or both comprising a polysiloxane that is at least 99% poly(dimethylsiloxane) elastomer; and
   a chamber located between the anterior face and the posterior face and comprising a silicone oil comprising polysiloxanes comprising diphenyl siloxane and dimethyl siloxane units and having a mean molecular weight of less than about 3000 Daltons.

9. The IOL of claim 8, wherein the polysiloxanes comprise at least about 30 mole % diphenyl siloxane.

10. The IOL of claim 8, further comprising an elastic side wall extending across the equator and extending from the anterior face to the posterior face.

* * * * *

UNITED STATES PATENT AND TRADEMARK OFFICE
CERTIFICATE OF CORRECTION

PATENT NO. : 11,357,618 B2
APPLICATION NO. : 17/378681
DATED : June 14, 2022
INVENTOR(S) : Forrest J. Ellis Page 1 of 1

It is certified that error appears in the above-identified patent and that said Letters Patent is hereby corrected as shown below:

On the Title Page

Item (73) Assignee:
Reads "JelliSee Orphthalmics Inc. , McLean, VA, (US)"
Should read --JelliSee Ophthalmics Inc., McLean, VA, (US)--

Signed and Sealed this
Thirtieth Day of August, 2022

Katherine Kelly Vidal
*Director of the United States Patent and Trademark Office*